United States Patent [19]

Berkoz et al.

[11] 4,064,135
[45] Dec. 20, 1977

[54] CERTAIN THIAZOLE-5-CARBOXAMIDE COMPOUNDS

[75] Inventors: Belig M. Berkoz, Los Altos; Brian Lewis, Mountain View, both of Calif.; Joseph M. Muchowski, Mexico D.F., Mexico

[73] Assignee: Syntex (U.S.A.) Inc., Palo Alto, Calif.

[21] Appl. No.: 706,412

[22] Filed: July 19, 1976

[51] Int. Cl.$^2$ .................................................. C07D 227/56
[52] U.S. Cl. ............................. 260/302 S; 260/302 R; 260/302 H
[58] Field of Search ........................ 260/302 R, 302 S

[56] References Cited

U.S. PATENT DOCUMENTS

| | | | |
|---|---|---|---|
| 3,230,229 | 1/1966 | Hatchard | 260/302 S |
| 3,668,212 | 6/1972 | Shen et al. | 260/302 S |
| 3,679,695 | 7/1972 | Moore et al. | 260/302 S |
| 3,888,870 | 6/1975 | Jackson | 260/302 S |

*Primary Examiner*—R. Gallagher
*Attorney, Agent, or Firm*—Gerard A. Blaufarb; Alan M. Krubiner

[57] ABSTRACT

Processes and intermediates for preparing 1-alkylamino-3-(5-substitutedaminocarbonylthiazol-2-yloxy)-2-propanols and 5-(5-substitutedaminocarbonyl-thiazol-2-yloxymethylene)-N-alkyloxazolidine and 2-substituted oxazolidine derivatives thereof and intermediates therefore. The present processes, and intermediates, reduce the number of transformations necessary to produce these products as compared with the prior processes. The products are useful to treat abnormal heart conditions and/or hypertension in mammals. The intermediates are 2-alkylsulfinyl-5-substitutedaminocarbonylthiazoles and 2-alkylsulfonyl-5-substitutedaminocarbonylthiazoles.

19 Claims, No Drawings

CERTAIN THIAZOLE-5-CARBOXAMIDE COMPOUNDS

BACKGROUND OF THE INVENTION

1. Field of the Invention

This invention relates to processes for preparing 1-alkylamino-3-(5-substitutedaminocarbonylthiazol-2-yloxy)-propan-2-ols and 3-(5-substitutedaminocarbonylthiazol-2-yloxy)-1,2-epoxypropanes; 5-(5-substitutedaminocarbonylthiazol-2-yloxymethylene)-N-alkyloxazolidines and derivatives thereof. In a further aspect this invention relates to 2-alkylsulfinyl-5-substituted aminocarbonylthiazoles and 2-alkylsulfonyl-5-substitutedaminocarbonylthiazoles and to processes for preparing such compounds.

2. The Prior Art

The present invention relates to improved processes and intermediates for preparing certain 1-alkylamino-3-(5-substitutedaminocarbonylthiazol-2-yloxy)-propan-2-ol β-blocking cardiovascular agents. These cardiovascular agents are typically prepared by a multistep process (note U.S. Pat. Nos. 3,896,139 and 3,897,441) requiring the conversion of the appropriate 2-halothiazole (or 5-substituted 2-halothiazole) to the corresponding thiazol-2-yloxy propanediol acetonide; thence to the diol; then to the mesylate and then finally to the corresponding 3-(5-substitutedaminocarbonylthiazol-2-yloxy)-1,2-epoxypropane which is then easily converted to the final product via treatment with the desired alkylamine. In contrast to this, the 1,2-epoxypropane intermediate is prepared in the present process, in a single step either directly from the corresponding 2-halothiazole or from the corresponding 2-sulfinyl or 2-sulfonylthiazole. The present invention also relates to improved processes for preparing certain 5-(thiazol-2-yloxymethylene)-N-alkyloxazolidines and derivatives thereof, which can be conducted at lower temperatures and afford purer products than the prior art processes described in the aforementioned U.S. patents.

SUMMARY OF THE INVENTION

In summary the compounds of the invention can be represented by the following generic formula:

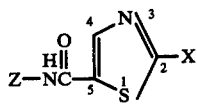

(I)

wherein X is the group —SOR$^1$ or —SO$_2$R$^1$ wherein R$^1$ is lower alkyl, phenyl, or benzyl and Z is selected from the group of alkyl having from one through 12 carbon atoms, and groups having the formulas:

R$^2$—(CH$_2$)$_m$—;

R$^3$ (CH$_2$)$_n$—;

R$^4$—CH=CH—(CH$_2$)$_n$—;

R$^5$—C≡C—(CH$_2$)$_n$— wherein m is 1, 2, 3, or 4; n is 2, 3, or 4; R$^2$ is cycloalkyl having from three through eight carbon atoms; R$^3$ is selected from the group of bicyclo [3.1.0]hexyl; bicyclo [2.2.1]heptyl; adamantyl; and 4-methylbicyclo [2.2.2]oct-1-yl and wherein attachment to the (CH$_2$)$_n$ linking group can be at any ring atom of bicyclo [3.1.0]hexyl; bicyclo [2.2.1]heptyl and adamantyl group and is at the 1-position of the 4-methylbicyclo [2.2.2]octyl group; and R$^4$ and R$^5$ are hydrogen or alkyl having from one through four carbon atoms and wherein the groups R$^4$—CH=CH—(CH$_2$)$_n$— and R$^5$—C≡C—(CH$_2$)$_n$— each have from four through eight carbon atoms.

In summary the processes of the invention for preparing the compounds, of the invention, comprises oxidizing the corresponding 5-substitutedaminocarbonyl-2-alkylthiothiazole to the corresponding 2-sulfinyl or 2-sulfonyl compound of formula I.

In summary the processes of the invention for preparing 5-substitutedaminocarbonylthiazol-2-yloxy 1,2-epoxypropanes comprise reacting the corresponding compound of formula I with glycidol anion. In summary the processes for preparing the 1-alkylamino-5-substitutedaminocarbonylthiazol-2-oxy propan-2-ol, comprise the additional step of reacting the 1,2-epoxypropane intermediate with the desired alkylamine.

In summary the processes for preparing 5-(5-substituted-aminocarbonylthiazol-2-yloxymethylene)-N-alkyloxazolidine and derivatives thereof comprise condensing the corresponding compound of formula I with the desired 5-hydroxymethyl-3-lower alkyloxazolidine or 2-mono or 2,2-dialkyl derivative thereof The invention will be further described hereinbelow.

FURTHER DESCRIPTION OF THE INVENTION AND PREFERRED EMBODIMENTS

The compounds of the invention can be represented by the following subgeneric formulas:

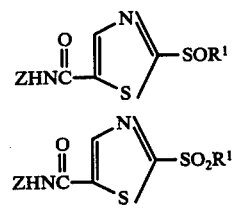

wherein R$^1$ is lower alkyl, phenyl, or benzyl and Z is selected from the group of alkyl having from one through 12 carbon atoms, and groups having the formula R$^2$—(CH$_2$)$_m$—;

R$^3$(CH$_2$)$_n$—;

R$^4$—CH=CH—(CH$_2$)$_n$—;

R$^5$—C≡C—(CH$_2$)$_n$— wherein m is 1, 2, 3, or 4; n is 2, 3, or 4; R$^2$ is cycloalkyl having from three through eight carbon atoms; R$^3$ is selected from the group of bicyclo [3.1.0]hexyl; bicyclo[2.2.1]heptyl; adamantyl; and 4-methylbicyclo[2.2.2]oct-1-yl and wherein attachment to the (CH$_2$)$_n$ linking group can be at any ring atom of bicyclo [3.1.0]hexyl; bicyclo [2.2.21]heptyl and adamantyl group and is at the 1-position of the 4-methylbicyclo [2.2.2]octyl group; and R$^4$ and R$^5$ are hydrogen or alkyl having from one through four carbon atoms and wherein the groups R$^4$—CH=CH—(CH$_2$)$_n$— and R$^5$—C≡C—(CH$_2$)$_n$— each have from four through eight carbon atoms.

Where the Z substituent contains asymmetric carbon, the compounds exist as optical isomers. The endo and exo forms of $R^3$ are geometric isomers as are also the cis and trans forms of the group $R^4-CH=CH-(CH_2)_n-$. Correspondingly the above formulas are intended to represent both the individual enantiomers and diastereomers as well as mixtures thereof and both the respective individual isomers as well as mixtures thereof are encompassed within the invention.

DEFINITIONS

As used hereinabove and below, the following terms have the following meanings unless expressly stated to the contrary. The term alkyl refers to both straight and branched chain alkyl groups. The term lower alkyl refers to both straight and branched chain alkyl groups having a total of from one through six carbon atoms and thus includes primary, secondary, and tertiary alkyl groups. Typical lower alkyls include, for example, methyl, ethyl, n-propyl, isopropyl, n-butyl, t-butyl, n-hexyl and the like.

The term alkenyl refers to unsaturated alkyl groups having a double bond (e.g. $CH_3CH=CH(CH_2)_2-$) and includes both straight and branched chain alkenyl groups. Typical alkenyl groups include, for example, but-3-enyl (i.e. $H_2C=CH(CH_2)_2-$); hex-4-enyl (i.e. $CH_3CH=CH(CH_2)_3-$); 5,5-dimethylhex-3-enyl $$\text{(i.e. } CH_3\overset{\overset{\displaystyle CH_3}{|}}{\underset{\underset{\displaystyle CH_3}{|}}{C}}HCH=CH(CH_2)_2-\text{); 6-methylhept-4-enyl}$$

$$\text{(i.e. } CH_3\overset{\overset{\displaystyle CH_3}{|}}{C}H_2CH=CH(CH_2)_3-\text{);}$$

oct-5-enyl (i.e. $C_2H_5CH=CH(CH_2)_4-$) and the like. The terms cis and trans refer to the following orientations:

$$\underset{\text{trans}}{\overset{H}{\underset{R^4}{\diagdown}}C=C\overset{(CH_2)_n-}{\underset{H}{\diagup}}} \quad \underset{\text{cis}}{\overset{R^4}{\underset{H}{\diagdown}}C=C\overset{(CH_2)_n-}{\underset{H}{\diagup}}}$$

The term alkynyl refers to unsaturated alkyl groups having a triple bond (e.g. $CH_3C\equiv C(CH_2)_2-$) and includes both straight and branched chain alkynyl groups. Typical alkynyl groups include, for example, but-3-ynyl (i.e. $HC\equiv C(CH_2)_2-$); hex-4-ynyl (i.e. $CH_3C\equiv C(CH_2)_3-$); 5,5-dimethylhex-3-ynyl $$\text{(i.e. } CH_3\overset{\overset{\displaystyle CH_3}{|}}{\underset{\underset{\displaystyle CH_3}{|}}{C}}HC\equiv C(CH_2)_2-\text{); 6-methylhept-4-ynyl}$$

$$\text{(i.e. } CH_3CH_2\overset{\overset{\displaystyle CH_3}{|}}{C}\equiv C(CH_2)_3-\text{);}$$

oct-5-ynyl (i.e. $C_2H_5C\equiv C(CH_2)_4-$) and the like.

The term alkylamino refers to the group having the formula $R'HN-$ wherein $R'$ is alkyl and the term lower alkylamino refers to such groups wherein $R'$ is lower alkyl.

The term aminocarbonyl or carbamoyl refers to the group having the formula $$H_2N\overset{\overset{\displaystyle O}{\|}}{C}.$$

The term substituted aminocarbonyl or substituted carbamoyl refers to the group having the formula $$ZNH\overset{\overset{\displaystyle O}{\|}}{C}-$$
wherein Z is as defined herein.

Typical substituted aminocarbonyl or substituted carbamoyl groups include, for example, 2-(endobicyclo[3.1.0]hex-6-yl)ethylaminocarbonyl or 2-(endobicyclo[3.1.0]hex-6-yl)ethylcarbamoyl; 4-(adamant-1-yl)-n-butylaminocarbonyl or 4-(adamant-1-yl)n-butylcarbamoyl; 5-methylhexylaminocarbonyl, cyclopentylethylaminocarbonyl, hex-5-ynylaminocarbonyl, 5-methylhex-3-ynylaminocarbonyl, hex-5-ynylaminocarbonyl, oct-5-cis-enylaminocarbonyl, 5,5-dimethylhex-cis-3-enylaminocarbonyl, oct-5-trans-enylaminocarbonyl and the like.

The term bicyclo [3.1.0]hexyl refers to, and encompasses, the following structural formulas, and the radicals represented thereby, and wherein the open substituent represents the point of attachment to the $$-(CH_2)_n\overset{\overset{\displaystyle H}{|}}{N}\overset{\overset{\displaystyle O}{\|}}{C}-$$

substituent of formula I:

exobicyclo[3 . 1 . 0]hex-6-yl   endobicyclo[3 . 1 . 0]hex-6-yl exobicyclo[3 . 1 . 0]hex-3-yl   endobicyclo[3 . 1 . 0]hex-3-yl exobicyclo[3 . 1 . 0]hex-2-yl*  endobicyclo[3 . 1 . 0]hex-2-yl* bicyclo[3 . 1 . 0]hex-1-yl*
*contains asymmetric carbon atom

The term bicyclo [2.2.1]heptyl, refers to, and encompasses, the following structural formulas, and the radicals represented thereby, and wherein the open substituent represents the point of attachment to the

substituent of formula I.

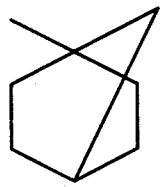
bicyclo[2.2.1]hept-1-yl

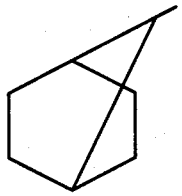
bicyclo[2.2.1]hept-7-yl

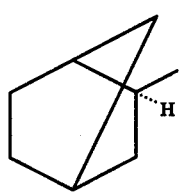
exobicyclo[2.2.1]hept-2-yl*
*contains asymmetric carbon atom

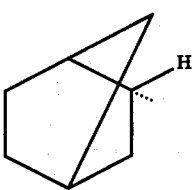
endobicyclo[2.2.1]hept-2-yl*

The term 4-methylbicyclo [2.2.2]oct-1-yl refers to the following structural formula and the radical represented thereby, wherein the open substituent represents the point of attachment to the

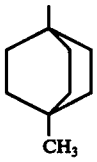

The term adamantyl refers to, and encompasses, the following structural formulas, and the radicals represented thereby, and wherein the open substituent represents the point of attachment to the

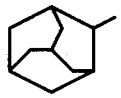
adamant-2-yl

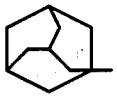
adamant-2-yl

Typical illustrations of the compounds of formula I can be had, for example, hereinbelow by reference to Examples 1, 2, and 2A. The preferred Z substituents are 2-(endobicyclo[3.1.0]hex-6-yl)ethyl, 2-cyclohexylethyl, 5-methylhex-3-ynyl and 5-methylhexyl. The preferred $R^1$ substitutents are methyl, ethyl, benzyl or phenyl and especially ethyl and benzyl.

The process of the invention for preparing the compounds of formula I can be represented by the following schematic overall reaction sequence.

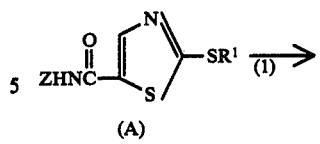

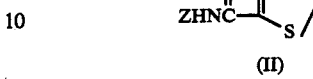

wherein $R^1$ and Z are as defined hereinabove.

Steps 1 and 2 are both oxidation steps and generally can be conducted as a single step. The oxidation can, for example, be conducted by treating the compound of formula (A) with hydrogen peroxide using acetic acid as a solvent. Where the compound of formula II is desired, the treatment is typically conducted at temperatures in the range of about from 20° to 60° C, preferably about from 40° to 50° C, for about from 10 minutes to 6 hours, preferably about from 2 to 3 hours, using a mole ratio of hydrogen peroxide to starting material of formula A of about from one to 10, preferably about from one to two. Other suitable solvents which can be used include, for example, acetone, chloroform, methylene, chloride and the like. Where the compounds of formula III are desired, the treatment is typically conducted at temperatures in the range of about from 20° to 70° C, preferably about from 30° to 55° C, for about from 5 to 20 hours, preferably about from six to 12 hours, using a mole ratio of hydrogen peroxide to starting material of formula A of about from two to 10, preferably from six to eight. Also in place of acetic acid, the following solvents can, for example, be used, acetone, chloroform, methylene chloride and the like. The compounds of formula II can be similarly conveniently oxidized to the compounds of formula III by treatment with hydrogen peroxide in acetic acid. In this case, the treatment is typically conducted at temperatures in the range of about from 40° to 70° C, preferably about from 50° to 60° C for about from 1 to 4 hours, using mole ratios of hydrogen peroxide to formula II of from bout two to 10, preferably from six to eight. Also other conventional oxidation systems could be used in place of the hydrogen peroxide system, for example, perbenzoic acid, peracetic acid, m-chloroperbenzoic acid, sodium periodate, and the like. In the case of the compounds of formula III wherein Z is $R^4$—CH=CH—$(CH_2)_n$— poor results are generally obtained using the hydrogen peroxide treatment described above, hence these compounds are best prepared via oxidation of the corresponding compound of formula A with sodium periodate in a suitable solvent-system. Typically this oxidation is conducted at temperatures in the range of about from 45° to 75° C, preferably about from 55° to 65° C, for about from 8 to 40 hours, preferably about from 15 to 20 hours using mole ratios of sodium periodate to compound of formula A in the range of about from two to ten, preferably about from two to three. Suitable solvents for the compounds of formula A which can be used include, for example, acetic acid, lower alkanols, e.g. methanol, ethanol, etc., and the like. Conveniently, water is used as the solvent for the sodium periodate. Hence, the solvent system will be water plus the particular inert organic solvent used for the compound of formula A. Typically the product of this oxidation is a major-minor mixture of both the compounds of formulas II and III, respectively, which can be used, without separation, as starting material to prepare the corresponding 1,2-epoxypropane compound of formula B in the process described hereinbelow. If desired, however, the respective products can be separated by column chromatography (e.g. silica gel) or on a laboratory scale by thin layer chromatography such as, for example, described in Example 2A hereinbelow.

The compound of formula II can be produced as the major product of the sodium periodate oxidation by reducing the reaction temperature (e.g. 25°–35° C).

The starting materials of formula A can be prepared by treating the 2-alkylthiothiazole or 2-benzylthiazole with butyl lithium followed by carbon dioxide to yield the corresponding lithium salt of 2-alkylthio- or 2-benzylthio-5-carboxythiazole. This lithium salt is allowed to react, for example, with ethylchloroformate or oxalyl chloride. The mixed anhydride or acid chloride is then heated with the appropriate monoamine (see Preparations 2 and 3 hereinbelow). The monoamines are known compounds or can be prepared by obvious adaptations of known procedures. Note, for example, the amine preparations described in U.S. application Ser. No. 706,342, pages 22–44 by Lewis, Unger and Untch and U.S. applications Ser. Nos. 706,341 and 706,413, pages 20–22 and 21–23, respectively by Berkoz, Lewis and Unger, all filed on even date herewith and hereby incorporated by reference. The 2-alkyl-thiazole or 2-benzylthiazole starting materials can be prepared by treating 2-bromothiazole or 2-chlorothiazole with the desired alkanethiol or benzylthiol and sodium hydride (see Preparation 1 hereinbelow).

Where desired the individual geometric isomers of formula I can be obtained by conventional separation and purification procedures.

The process, of the invention, for preparing the 1,2-epoxypropane thiazole intermediates and the process of the invention for preparing the 1-alkylamino-3-(5-substituted-aminocarbonylthiazol-2-yloxy)-2-propanol cardiovascular agents can be schematically represented by the following overall reaction sequence:

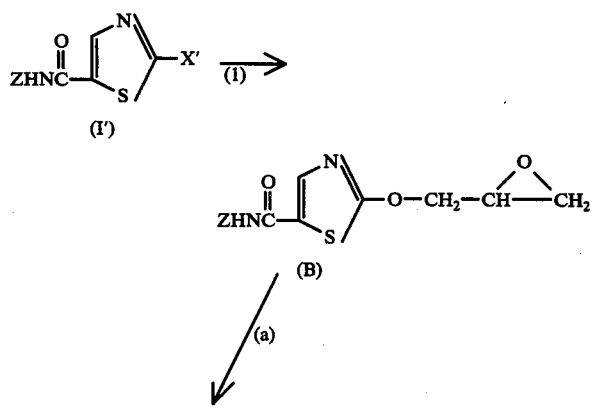

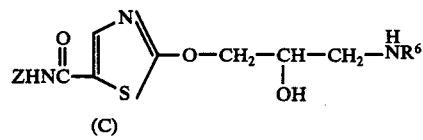

(C)

wherein X' is bromo, chloro, —SOR$^1$ or —SO$_2$R$^1$, wherein R$^1$ is lower alkyl, phenyl or benzyl; R$^6$ is lower alkyl; and Z is as defined hereinabove.

Step 1 can be effected by treating the compound of formula I' with glycidol anion in an inert organic solvent. This treatment is conveniently conducted by first treating glycidol with an alkali metal hydride to generate the glycidol anion. This initial treatment is typically conducted at temperatures in the range of about from −30° to 30° C, preferably about from −10° to 5° C for about 1 minute to 1 hour, preferably about from 5 minutes to 20 minutes. The compound of formula I', typically dissolved in an inert organic solvent, can then be treated with the preceding glycidol anion mixture. Typically, this treatment is conducted at temperatures in the range of about from −30° to 25° C, preferably about from −10° to 0° C, for about from 1 minute to 1 hour, preferably about from 10 to 30 minutes. Typically, mole ratios of glycidol to alkali metal hydride of about from 1–5:1 are used, preferably about from 1.0 to 1.3:1, and mole ratios of glycidol to compound of formula I' in the range of about from 1 to 5, preferably about from 1.0 to 1.3 are used. Suitable alkali metal hydrides which can be used include, for example, sodium hydride, potassium hydride, lithium hydride, and the like. Suitable inert organic solvents which can be used include, for example, tetrahydrofuran, diethyl ether, dioxane, dimethoxyethane, dimethylformamide and the like, and mixtures thereof. Both procedures of the treatment are conducted under anhydrous conditions, and preferably under an inert atmosphere (e.g. nitrogen). The resulting product of formula B is preferably isolated before being used as starting material for the next step. Such isolation can be effected by conventional separation procedures such as, for example, precipitation with water, extraction, crystallization or chromatography. Illustrations of typical separation and isolation procedures can be had by reference to Examples 3 and 4, hereinbelow.

The 2-bromo- or 2-chloro-5-substituted aminocarbonylthiazole starting material of formula I' can be prepared by treating 2-bromo- or 2-chloro-5-carboxythiazole with ethylchloroformate or oxalyl chloride followed by treatment with the desired primary amine.

The products of formula C can be conveniently prepared by treating the compound of formula B with a monoalkylamine having the desired alkyl substituent. Typically, this treatment is conducted in an inert organic solvent and is typically conducted at temperatures in the range of about from −10° to 100° C, preferably about from 10° to 25° C, for about from 1 hour to 48 hours, preferably about from 5 to 18 hours. Typically about from one to 30 moles, preferably about from 1 to 10 moles of alkylamine to compound of formula B is used. Suitable alkylamines which can be used include, for example, methylamine, ethylamine, isopropylamine, t-butylamine, n-pentylamine, 4-methylpentylamine and the like. Suitable inert organic solvents which can be used include, for example, methanol, ethanol, monoglyme, acetone and the like and mixtures thereof. The resulting products of formula C can then be separated and isolated according to conventional procedures such as, for example, evaporation, crystallization, chromatography, thin-layer chromatography, etc. Specific illustrations of typical separation and isolation procedures can be had by reference to the corresponding examples, set forth hereinbelow.

A further embodiment of the invention comprises an improved process for preparing the cardiovascular agents represented by formula (E) below. This process can be schematically represented by the following overall reaction equation.

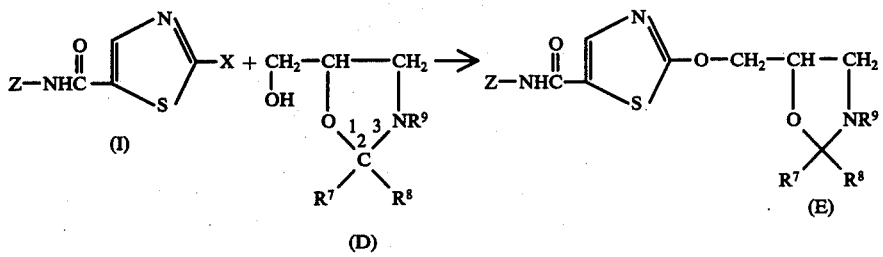

wherein $R^9$ is lower alkyl; $R^7$ and $R^8$ are independently hydrogen or lower alkyl; and X and Z are as defined hereinabove.

This process is preferably conducted in two steps. In the initial step the 5-hydroxymethyl-3-lower alkyl-oxazolidone or 2-mono or 2,2-dialkyl derivative thereof (formula D) is treated with an alkaline metal hydride, e.g. sodium hydride, in a suitable inert organic solvent. Typically, this treatment is conducted at temperatures in the range of about from −5° to 100° C, preferably about from 25° to 60° C, for about 10 minutes to 6 hours, preferably about from 1 hour to to 3 hours. Suitable inert organic solvents which can be used include, for example, tetrahydrofuran, dimethylformamide, monoglyme, diglyme, and the like. The second step can be effected by treating the initial product reaction mixture with the starting material of formula I having the 5-position substituent desired in the product. Typically, this treatment is conducted at temperatures in the range of about from −20° to 80° C, preferably about from 0° to 30° C, for about from 1 minute to 10 hours, preferably about from 5 minutes to 2 hours. Typically, the compound of formula I is added to the reaction mixture in the form of a solution in a suitable inert organic solvent. Suitable inert organic solvents which can be used include, for example, tetrahydrofuran, dimethylformamide, monoglyme, diglyme, and the like. Also, in some instances, an excess of the oxazolidine reagent can be used as the solvent. Both steps of this procedure are conducted under anhydrous conditions and preferably are conducted in an inert gas such as, for example, nitrogen.

The product of formula E can then be separated and purified according to conventional procedures such as, for example, illustrated in Example 7, hereinbelow. Care should be exercised during the purification procedure as the compounds of formula E are easily hydrolyzed to the compounds of 1-alkylaminopropan-2-ol compounds of formula C, described hereinbelow, under both acid and basic conditions. Correspondingly, the alkylamino compounds of formula C can be readily prepared by simple acid or base hydrolysis of the corresponding compounds of formula E. Acid hydrolysis can be conveniently effected by treating the compound of formula E with a suitable organic acid such as, for example, acetic, formic, oxalic acid and the like or suitable inorganic acid such as, for example, hydrochloric, sulfuric, and the like. Preferably the hydrolysis is conducted under midly acidic conditions. Similarly, basic hydrolysis can be conducted by treating the compound of formula E with a suitable base such as, for example, dilute sodium hydroxide, potassium hydroxide and the like. Preferably the base hydrolysis is conducted under midly alkaline conditions. Alternatively, the hydrolysis can be conducted via exchange with a suitable ion exchange resin in either the H+ or OH− form.

If desired the pharmaceutically acceptable acid addition salts of the products of formula C can be prepared from the parent compound, typically via neutralization of an amino moiety, with the desired acid. Other pharmaceutically acceptable addition salts can then be conveniently prepared from the addition salts via anion exchange with a suitable ion exchange resin in the desired anionic form.

The compounds of formulas C and E, and their pharmaceutically acceptable salts (e.g. hydrochloride, maleate, etc.) are useful in the treatment and palliation of cardiovascular abnormalities in mammals. These compounds primarily achieve their therapeutic action by selectively blocking the cardiac β-adrenergic receptor sites and, accordingly, because they are cardiac selective, they can also be applied to treat cardiac abnormalities in patients suffering from asthma or chronic obstructive lung disease. Further, based on the virtual identity of therapeutic activity, observed between the counterparts of formulas C and E, and the fact that the compounds of formula E are readily hydrolyzed to the compounds of formula C, it is believed that the compounds of formula E hydrolyze in vivo and hence function therapeutically as the compounds of formula C. The compounds are especially useful in the treatment or palliation of cardiac arrhythmias, angina pectoris, hypetrophic subaortic stenosis, pheochromocytoma, thyrotoxicosis, hyperkinetic syndromes, tetralogy of Fallot, mitral stenosis with tachycardia, general ischemic conditions, and hypertension founded on elevated cardiac outputs due to a hyperadrenergic state. The compounds are active, both in the treatment or palliation of acute attacks of such cardiac disorders, and further can be applied prophylactically to prevent or reduce the frequency of such attacks. This prophylactic action is particularly desirable in reducing the frequency of attacks of angina pectoris, since the medication (i.e. nitroglycerin) presently commonly used in the treatment of angina pectoris has no recognized prophylactic action. Additional information concerning the use, action and determination of β-blockers can be obtained, by reference to the literature such as, for example, Dotlery et al, *Clinical Pharmacology and Therapeutics*, volume 10, no. 6, 765–797 and the references cited therein.

These compounds are also useful in the treatment of hypertension in mammals.

Whether administered for the treatment of cardiac disorders or hypertersion, the compounds are typically administered in dosages of about from 0.01 to 5 mg. per kg. of body weight. The precise effective dosage will, of course, vary depending upon the mode of administration, the condition being treated and the host. Where the compounds are used to treat cardiac conditions such as arrhythmias, the compounds are typically administered either orally or intravenously. Where the compounds are administered to treat hypertension or cardiac conditions such as angina pectoris, the compounds are, for the sake of convenience, typically administered orally.

These compounds can be administered for the treatment of cardiac disorders and hypertension in a wide variety of dosage forms, either alone or in combination with other pharmaceutically compatible medicaments, in the form of pharmaceutical compositions suited for oral or parenteral administration. The compounds are typically administered as pharmaceutical compositions consisting essentially of the compounds of the invention and a pharmaceutical carrier. In the case of the compounds of formula C, the compounds are typically administered as pharmaceutically acceptable salts. The pharmaceutical carrier can be either a solid material or liquid, in which the compound is dissolved, dispersed or suspended, and can optionally contain small amounts of preservatives and/or pH-buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups or elixirs and optionally can contain small quantities of preservatives and/or buffering agents, and preferably contain the therapeutic agent in convenient unit dosage concentrations.

The solid compositions can take the form of tablets, powders, capsules, pills or the like, preferably in unit dosage forms for simple administration or precise dosages. Suitable solid carriers include, for example, pharmaceutical grades of starch, lactose, sodium saccharin, sodium bisulfite and the like.

A further understanding of the invention can be had from the following non-limiting Preparations and Examples. Also as used hereinabove and below unless expressly stated to the contrary, all temperatures and temperature ranges refer to the Centrigrade system and the terms ambient or room temperature refer to about 20° C. The term percent or (%) refers to weight percent and the term mole or moles refers to gram moles. The term equivalent refers to a quantity of reagent equal in moles to the moles of the preceding or succeeding reactant recited in that Preparation or Example in terms of moles or finite weight or volume. Also unless expressly stated to the contrary, racemic mixtures and/or diastereomer mixtures are used as starting materials and correspondingly racemic mixtures and/or diastereomer mixtures are obtained as products and where necessary, preparations and examples are repeated to provide sufficient quantities of starting materials for subsequent preparations and examples. Where given proton magnetic resonance spectrum (n.m.r.) are determined at 100 mHz (the signs of the coupling constants are not assigned) and signals are assigned as singlets (s), broad singlets (bs), doublets (d), double doublets (dd), triplets (t), double triplets (dt), quartets (q) and multiplets (m).

PREPARATION 1

2-Ethylthiothiazole

In this preparation 0.15 mole of 50% sodium hydride in mineral oil is stirred in 100 ml. of dimethylformamide, under a nitrogen atmosphere, then cooled to −50° C and 0.15 mole of ethanethiol (i.e. ethylmercaptan) is added dropwise. The resulting mixture is warmed to 0° C and then recooled to −50° C and 0.1 mole of 2-bromothiazole (K. Ganapathi et al, *Proc. Indian Acad. Sci., A*22, 362 (1945)) is added. The resulting mixture is warmed to room temperature (about 20° C) and maintained at this temperature until the reaction is determined to be complete as shown by thin-layer chromatography; about two hours. The mixture is then poured into 500 ml. of hexane, then washed three times with water. The organic layer is dried with anhydrous magnesium sulfate, filtered, and the resulting filtrate evaporated under vacuum yielding 2-ethylthiothiazole as a colorless oil.

Similarly by following the same procedure but respectively using methyl mercaptan, t-butylmercaptan, hexyl mercaptan and benzyl mercaptan in place of ethanethiol, 2-methylthiothiazole; 2-t-butylthiothiazole; 2-hexylthiothiazone and 2-benzylthiothiazole are respectively prepared.

PREPARATION 2

2-Ethylthio-5-carboxythiazole

In this preparation 0.2 mole of 2-ethylthiothiazole is dissolved in 300 ml. of anhydrous tetrahydrofuran, under a nitrogen atmosphere, then cooled to −80° C. 0.2 Mole of butyl lithium in 125 ml. of hexane is then added dropwise with stirring. The mixture is stirred for five minutes and then anhydrous carbon dioxide bubbled through the mixture until reaction is completed (the reaction is monitored by thin-layer chromatography). The mixture is allowed to warm to 0° C, 300 ml. of hexane added and then filtered. The filter cake is recovered and washed with ethyl ether, affording the lithium salt of 2-ethylthio-5-carboxythiazole, and then slurried with 300 ml. of ethyl acetate. The ethyl acetate slurry is then acidified with 2 Normal hydrochloric acid and washed with water. The organic layer is recovered, dried with anhydrous magnesium sulfate, and the resulting filtrate evaporated to dryness under vacuum yielding 2-ethylthio-5-carboxythiazole.

Similarly by following the same procedure, but using the remaining products prepared according to Preparation 1, the corresponding 2-alkyl and 2-benzyl-5-carboxythiazoles are respectively prepared.

PREPARATION 3

2-Alkylthio-5-substituted aminocarbonylthiazole

In this preparation 0.1 mole of 2-ethylthio-5-carboxythiazole is dissolved in 300 ml. of anhydrous tetrahydrofuran, under nitrogen, and 0.1 mole of triethylamine is added and the resulting mixture cooled to −30° C. 0.1 Mole of ethylchloroformate is then added dropwise with stirring and the resulting mixture allowed to warm to 0° C. The mixture is then stirred for ten minutes, then cooled to −30° C and 0.11 mole of 2-(bicyclo[2.2.1]-hept-7-yl)ethylamine in 50 ml. of tetrahydrofuran added dropwise. The mixture is allowed to warm to room temperature (about 20° C), poured into 500 ml. of ethyl acetate, washed with water, then washed with saturated aqueous sodium chloride solution, and dried over anhydrous magnesium sulfate. The mixture is then filtered and the resulting filtrate evaporated under vacuum yielding 2-ethylthio-5-[2-(bicyclo[2.2.1]hept-7-yl)ethylaminocarbonyl]-thiazole as a solid, which is then further purified by recrystallization from ethyl acetate.

Similarly by following the same procedure but respectively using the amines listed in Table A, hereinbelow, in place of 2-(bicyclo[2.2.1]hept-7-yl)ethylamine, the corresponding 5-substituted aminocarbonylthiazole analogs are respectively prepared:

TABLE A 2-(bicyclo[2.2.1]hept-1-yl)ethylamine;
2-(exobicyclo[2.2.1]hept-2-yl)ethylamine;
2-(endobicyclo[2.2.1]hept-2-yl)ethylamine;
2-(exobicyclo[3.1.0]hex-6-yl)ethylamine;
2-(endobicyclo[3.1.0]hex-6-yl)ethylamine;
2-(exobicyclo[3.1.0]hex-3-yl)ethylamine;
2-(endobicyclo[3.1.0]hex-3-yl)ethylamine;
2-(exobicyclo[3.1.0]hex-2-yl)ethylamine;
2-(endobicyclo[3.1.0]hex-2-yl)ethylamine;
2-(bicyclo[3.1.0]hex-1-yl)ethylamine;
2-(4-methylbicyclo[2.2.2]oct-1-yl)ethylamine;
2-(adamant-2-yl)ethylamine;
2-(adamant-1-yl)ethylamine;
3-(bicyclo[2.2.1]hept-7-yl)n-propylamine;
3-(exobicyclo[3.1.0]hex-6-yl)n-propylamine;
3-(endobicyclo[3.1.0]hex-6-yl)n-propylamine;
3-(endobicyclo[3.1.0]hex-3-yl)n-propylamine;
3-(4-methylbicyclo[2.2.2]oct-1-yl)n-propylamine;
3-(adamant-2-yl)n-propylamine;
4-(bicyclo[2.2.1]hept-7-yl)n-butylamine;
4-(exobicyclo[2.2.1]hept-2-yl)n-butylamine;
4-endobicyclo[2.2.1]hept-2-yl)n-butylamine;
4-(endobicyclo[3.1.0]hex-6-yl)n-butylamine;
4-(endobicyclo[3.1.0]hex-3-yl)n-butylamine;
4-(exobicyclo[3.1.0]hex-2-yl)n-butylamine;
4-(4-methylbicyclo[2.2.2]oct-1-yl)n-butylamine;
4-(adamant-2-yl)n-butylamine;
4-(adamant-1-yl)n-butylamine;
1-aminohex-5-ene;
1-aminobut-3-ene;
1-aminopent-cis-3-ene;
1-aminohex-cis-3-ene;
1-aminohept-cis-3-ene;
1-amino-5-methylhex-cis-3-ene;
1-aminooct-cis-3-ene;
1-amino-6-methylhept-cis-3-ene;
1-amino-5,5-dimethylhex-cis-3-ene;
1-aminopent-4-ene;
1-amino-6-methylhept-cis-4-ene;
1-aminooct-cis-5-ene;
1-aminopent-trans-3-ene;
1-aminohex-trans-3-ene;
1-aminohept-trans-3-ene;
1-amino-5-methylhex-trans-3-ene;
1-aminooct-trans-3-ene;
1-amino-6-methylhept-trans-3-ene;
1-amino-5,5-dimethylhex-trans-3-ene;
1-aminohex-trans-4-ene;
1-aminooct-trans-4-ene;
1-aminohept-trans-5-ene;
1-aminobut-3-yne;
1-aminopent-3-yne;
1-aminohex-3-yne;
1-aminohept-3-yne;
1-amino-5-methylhex-3-yne;
1-aminooct-3-yne;
1-amino-6-methylhept-3-yne;
1-aminopent-4-yne;
1-aminohex-4-yne;
1-aminohept-4-yne;
1-aminooct-4-yne;
1-amino-6-methylhept-4-yne;
1-aminohex-5-yne;
1-aminohept-5-yne;
1-aminooct-5-yne;
1-amino-5,5-dimethylhex-3-yne;
methylamine;
t-butylamine;
hexylamine;
4-methylhexylamine;
5-methylhexylamine;
heptylamine;
3-propylheptylamine;
decylamine;
dodecylamine;
2-cyclopentylethylamine;
2-cyclohexylethylamine;
3-cyclopentylpropylamine;
4-cyclohexylbutylamine;
cycloheptylmethylamine; and
4-cyclooctylbutylamine.

Similarly, by following the same procedure but using the corresponding products of Preparation 2 as starting materials, the corresponding 2-methylthio; 2-t-butylthio; 2-hexylthio and 2-benzylthio analogs and each of the above compounds are respectively prepared.

PREPARATION 4

By following the procedure of Preparation 3 but respectively using 2-bromo-5-carboxythiazole and 2-chloro-5-carboxythiazole in place of 2-ethylthio-5-carboxythiazole, the 2-bromo and 2-chloro analogs of the products of Preparation 3 are respectively prepared.

EXAMPLE 1

This example illustrates the preparation of the compounds of formula I wherein X is $-SOR^1$. In this example a mixture of 20 g. of 2-ethylthio-5-[2-(bicyclo[2.2.1]-hept-7-yl)ethylaminocarbonyl]thiazole (0.064 mole); 40 ml. of 30% aqueous hydrogen peroxide and 200 ml. of acetic acid is stirred at a temperature of from 40° to 50° C for 4 hours. The mixture is concentrated by evaporation of a large portion of the acetic acid, under vacuum, at room temperature (about 20° C) and the resulting residue poured into 500 ml. of ethyl acetate and then washed with aqueous sodium bicarbonate solution until no acetic acid is present in the organic layer. The ethyl acetate layer is then separated, dried with anhydrous magnesium sulfate, filtered, and the resulting filtrate evaporated to dryness, under vacuum, affording 2-ethylsulfinyl-5-[2-(bicyclo[2.2.1]hept-7-yl)ethylaminocarbonyl]thiazole.

Similarly, by following the same procedure but respectively replacing 2-ethylthio-5-[2-(bicyclo[2.2.1]-hept-7-yl)ethyl aminocarbonyl]thiazole with the 2-ethylthio-5-substituted aminocarbonylthiazole products of Preparation 3, the following 2-ethylsulfinyl analogs are respectively prepared.

2-ethylsulfinyl-5-[2-(bicyclo[2.2.1]hept-1-yl)ethylamino-carbonyl]thiazole;

2-ethylsulfinyl-5-[2-(exobicyclo[2.2.1]hept-2-yl)ethylaminocarbonyl]thiazole;
2-ethylsulfinyl-5-[2-(endobicyclo[2.2.1]hept-2-yl)ethylaminocarbonyl]thiazole;
2-ethylsulfinyl-5-[2-(exobicyclo[3.1.0]hex-6-yl)ethylaminocarbonyl]thiazole;
2-ethylsulfinyl-5-[2-(endobicyclo[3.1.0]hex-6-yl)ethylaminocarbonyl]thiazole, nmr δ:1.29t, 3H; 1.65m, 11H; 3.30m, 4H; 6.80bs, 1H; 8.30s, 1H;
2-ethylsulfinyl-5-[2-(exobicyclo[3.1.0]hex-3-yl)ethylaminocarbonyl]thiazole;
2-ethylsulfinyl-5-[2-(endobicyclo[3.1.0]hex-3-yl)ethylaminocarbonyl]thiazole;
2-ethylsulfinyl-5-[2-(exobicyclo[3.1.0]hex-2-yl)ethylaminocarbonyl]thiazole;
2-ethylsulfinyl-5-[2-(endobicyclo[3.1.0]hex-2-yl)ethylaminocarbonyl]thiazole;
2-ethylsulfinyl-5-[2-(bicyclo[3.1.0]hex-1-yl)ethylaminocarbonyl]thiazole;
2-ethylsulfinyl-5-[2-(4-methylbicyclo[2.2.2]oct-1-yl)ethylaminocarbonyl]thiazole;
2-ethylsulfinyl-5-[2-(adamant-2-yl)ethylaminocarbonyl]thiazole, nmr (CDCl$_3$) δ: 1.30t, 3H; 1.76bs, 17H; 3.30m, 4H; 6.50bs, 1H; 8.27s, 1H;
2-ethylsulfinyl-5-[2-(adamant-1-yl)ethylaminocarbonyl]thiazole;
2-ethylsulfinyl-5-[3-(bicyclo[2.2.1]hept-7-yl)n-propylaminocarbonyl]thiazole;
2-ethylsulfinyl-5-[3-(exobicyclo[3.1.0]hex-6-yl)n-propylaminocarbonyl]thiazole;
2-ethylsulfinyl-5-[3-(endobicyclo[3.1.0]hex-6-yl)n-propylaminocarbonyl]thiazole;
2-ethylsulfinyl-5-[3-(endobicyclo[3.1.0]hex-3-yl)n-propylaminocarbonyl]thiazole;
2-ethylsulfinyl-5-[3-(4-methylbicyclo[2.2.2]oct-1-yl)n-propylaminocarbonyl]thiazole;
2-ethylsulfinyl-5-[3-(adamant-2-yl)n-propylaminocarbobnyl]thiazole;
2-ethylsulfinyl-5-[4-(bicyclo[2.2.1]hept-7-yl)n-butylaminocarbonyl]thiazole;
2-ethylsulfinyl-5-[4-(exobicyclo[2.2.1]hept-2-yl)n-butylaminocarbonyl]thiazole;
2-ethylsulfinyl-5-[4-(endobicyclo[2.2.1]hept-2-yl)n-butylaminocarbonyl]thiazole;
2-ethylsulfinyl-5-[4-(endobicyclo[3.1.0]hex-6-yl)n-butylaminocarbonyl]thiazole;
2-ethylsulfinyl-5-[4-(endobicyclo[3.1.0]hex-3-yl)n-butylaminocarbonyl]thiazole;
2-ethylsulfinyl-5-[4-(exobicyclo[3.1.0]hex-2-yl)n-butylaminocarbonyl]thiazole;
2-ethylsulfinyl-5-[4-(4-methylbicyclo[2.2.2]oct-1-yl)n-butylaminocarbonyl]thiazole;
2-ethylsulfinyl-5-[4-(adamant-2-yl)n-butylaminocarbonyl]thiazole;
2-ethylsulfinyl-5-[4-(adamant-1-yl)n-butylaminocarbonyl]thiazole;
2-ethylsulfinyl-5-(hex-5-enylaminocarbonyl)thiazole;
2-ethylsulfinyl-5-(but-3-enylaminocarbonyl)thiazole;
2-ethylsulfinyl-5-(pent-cis-3-enylaminocarbonyl)thiazole;
2-ethylsulfinyl-5-(hex-cis-3-enylaminocarbonyl)thiazole;
2-ethylsulfinyl-5-(hept-cis-3-enylaminocarbonyl)thiazole;
2-ethylsulfinyl-5-(5-methylhex-cis-3-enylaminocarbonyl)thiazole;
2-ethylsulfinyl-5-(oct-cis-3-enylaminocarbonyl)thiazole;
2-ethylsulfinyl-5-(6-methylhept-cis-3-enylaminocarbonyl)thiazole;
2-ethylsulfinyl-5-(5,5-dimethylhex-cis-3-enylaminocarbonyl)thiazole;
2-ethylsulfinyl-5-(pent-4-enylaminocarbonyl)thiazole;
2-ethylsulfinyl-5-(6-methylhept-cis-4-enylaminocarbonyl)thiazole;
2-ethylsulfinyl-5-(oct-cis-5-enylaminocarbonyl)thiazole;
2-ethylsulfinyl-5-(pent-trans-3-enylaminocarbonyl)thiazole;
2-ethylsulfinyl-5-(hex-trans-3-enylaminocarbonyl)thiazole;
2-ethylsulfinyl-5-(hept-trans-3-enylaminocarbonyl)thaizle;
2-ethylsulfinyl-5-(5-methylhex-trans-3-enylaminocarbonyl)thiazole;
2-ethylsulfinyl-5-(oct-trans-3-enylaminocarbonyl)thiazole;
2-ethylsulfinyl-5-(6-methylhept-trans-3-enylaminocarbonyl)thiazole;
2-ethylsulfinyl-5-(5,5,-dimethylhex-trans-3-enylaminocarbonyl)thiazole;
2-ethylsulfinyl-5-(hex-trans-4-enylaminocarbonyl)thiazole;
2-ethylsulfinyl-5-(oct-trans-4-enylaminocarbonyl)thiazole;
2-ethylsulfinyl-5-(hept-trans-5-enylaminocarbonyl)thiazole;
2-ethylsulfinyl-5-(but-3-ynylaminocarbonyl)thiazole;
2-ethylsulfinyl-5-(pent-3-ynylaminocarbonyl)thiazole;
2-ethylsulfinyl-5-(hex-3-ynylaminocarbonyl)thiazole;
2-ethylsulfinyl-5-(hept-3-ynylaminocarbonyl)thiazole;
2-ethylsulfinyl-5-(5-methylhex-3-ynylaminocarbonyl)thiazole;
2-ethylsulfinyl-5-(oct-3-ynylaminocarbonyl)thiazole;
2-ethylsulfinyl-5-(6-methylhept-3-ynylaminocarbonyl)thiazole;
2-ethylsulfinyl-5-(pent-4-ynylaminocarbonyl)thiazole;
2-ethylsulfinyl-5-(hex-4-ynylaminocarbonyl)thiazole;
2-ethylsulfinyl-5-(hept-4-ynylaminocarbonyl)thiazole;
2-ethylsulfinyl-5-(oct-4-ynylaminocarbonyl)thiazole;
2-ethylsulfinyl-5-(6-methylhept-4-ynylaminocarbonyl)thiazole;
2-ethylsulfinyl-5-(hex-5-ynylaminocarbonyl)thiazole;
2-ethylsulfinyl-5-(hept-5-ynylaminocarbonyl)thiazole;
2-ethylsulfinyl-5-(oct-5-ynylaminocarbonyl)thiazole;
2-ethylsulfinyl-5-(5,5,-dimethylhex-3-ynylaminocarbonyl)thiazole nmr (CDCl$_3$) δ:1.15d, 6H; 1.30t, 3H; 2.50t, 2H; 3.2m, 3H; 3.5t, 3H; 6.82bs, 1H; 8.30s, 1H;
2-ethylsulfinyl-5-(methylaminocarbonyl)thiazole;
2-ethylsulfinyl-5-(t-butylaminocarbonyl)thiazole;
2-ethylsulfinyl-5-(hexylaminocarbonyl)thiazole;
2-ethylsulfinyl-5-(4-methylhexylaminocarbonyl)thiazole;
2-ethylsulfinyl-5-(5-methylhexylaminocarbonyl)thiazole;
2-ethylsulfinyl-5-(heptylaminocarbonyl)thiazole;
2-ethylsulfinyl-5-(3-propylheptylaminocarbonyl)thiazole;
2-ethylsulfinyl-5-(decylaminocarbonyl)thiazole;
2-ethylsulfinyl-5-(dodecylaminocarbonyl)thiazole;
2-ethylsulfinyl-5-(cyclopentylethylaminocarbonyl)thiazole;
2-ethylsulfinyl-5-(2-cyclohexylethylaminocarbonyl)thiazole;

2-ethylsulfinyl-5-(3-cyclopentylpropylaminocarbonyl)-thiazole;
-ethylsulfinyl-5-(4-cyclohexylbutylaminocarbonyl)-thiazole;
2-ethylsulfinl-5-(cycloheptylmethylaminocarbonyl)-thiazole; and
2-ethylsulfinyl-5-(4-cyclooctylbutylaminocarbonyl)-thiazole.

Similarly, by following the same procedure but using the corresponding products of Preparation 3 as starting materials, the corresponding 2-methylsulfinyl; 2-t-butylsulfinyl; 2-hexylsulfinyl; and 2-benzylsulfinyl analogs of each of the above compounds are respectively prepared.

EXAMPLE 2

This example illustrated the preparation of the compounds of formula I wherein X is $-SO_2R^1$. In this example a mixture of 10 g. (0.028 mole) of 2-ethylthio-5-[2-(adamant-1-yl)ethylaminocarbonyl]thiazole; 20 ml. of 30% hyrogen peroxide and 100 ml. of acetic acid are heated at 75° C for 2 hours, most of the acetic acid is then removed by evaporation under vacuum and the resulting residue dissolved in 250 ml. of ethyl acetate and then washed with aqueous sodium bicarbonate solution until all traces of acetic acid are removed. The ethyl acetate layer is separated and then dried with anhyrous magnesium sulfate, filtered, and the resulting filtrate evaporated under vacuum to dryness affording 2-ethylsulfonyl-5-[2-(adamant-1-yl)ethylaminocarbonyl]thiazole, nmr (CDCl$_3$) δ:1.38t, 3H; 1.60m, 17H; 3.46m, 4H; 6.50bs, 1H; 8.28S, 1H;

Similarly, by following the same procedure but respectively replacing 2-ethylthio-5-[2-(adamant-1-yl)ethylaminocarbonyl]thiazole with the corresponding 2-ethylthio products of Preparation 3, the following 2-ethylsulfonyl analogs are respectively prepared:
2-ethylsulfonyl-5-[2-(bicyclo[2.2.1]hept-7yl)ethylaminocarbonyl]thiazole;
2-ethylsulfonyl-5-[2-(bicyclo[2,2,1]hept-1-yl)ethylaminocarbonyl]thiazole;
2-ethylsulfonyl-5-[2-(exobicyclo[2.2.1]hept-2-yl)ethylaminocarbonyl]thiazole;
2-ethylsulfonyl-5-[2-(endobicyclo[2.2.1]hept-2-yl)ethylaminocarbonyl]thiazole;
2-ethylsulfonyl-5-[2-(exobicyclo[3.1.0]hex-6-yl)ethylaminocarbonyl]thiazole;
2-ethylsulfonyl-5-[2-(endobicyclo[3.1.0]hex-6-yl)ethylaminocarbonyl]thiazole;
2-ethylsulfonyl-5-[2-(exobicyclo[3.1.0]hex-3-yl)ethylaminocarbonyl]thiazole;
2-ethylsulfonyl-5-[2-(endobicyclo[3.1.0]hex-3-yl)ethylaminocarbonyl]thiazole;
2-ethylsulfonyl-5-[2-(exobicyclo[3.1.0]hex-2-yl)ethylaminocarbonyl]thiazole;
2-ethylsulfonyl-5-[2-(endobicyclo[3.1.0]hex-2-yl)ethylaminocarbonyl]thiazole;
2-ethylsulfonyl-5-[2-(bicyclo[3.1.0]hex-1-yl)ethylaminocarbonyl]thiazole;
2-ethylsulfonyl-5-[2-(4-methylbicyclo[2.2.2]oct-1-yl)ethylaminocarbonyl]thiazole;
2-ethylsulfonyl-5-[2-(adamant-2-yl)ethylaminocarbonyl]-thiazole;
2-ethylsulfonyl-5-[3-(bicyclo[2.2.1]hept-7-yl)n-propylaminocarbonyl]thiazole;
2-ethylsulfonyl-5-[3-(exobicyclo[3.1.0]hex-6-yl)n-propylaminocarbonyl]thiazole;
2-ethylsulfonyl-5-[3-(endobicyclo[3.1.0]hex-6-yl)n-propylaminocarbonyl]thiazole;
2-ethylsulfonyl-5-[3-(endobicyclo[3.1.0]hex-3-yl)n-propylaminocarbonyl]thiazole;
2-ethylsulfonyl-5-[3-(4-methylbicyclo[2.2.2]oct-1-yl)n-propylaminocarbonyl]thiazole;
2-ethylsulfonyl-5-[3-(adamant-2-yl)n-propylaminocarbonyl]-thiazole;
2-ethylsulfonyl-5-[4-(bicyclo[2.2.1]hept-7-yl)n-butylaminocarbonyl]thiazole;
2-ethylsulfonyl-5-[4-(exobicyclo[2.2.1]hept-2-yl)n-butylaminocarbonyl]thiazole;
2-ethylsulfonyl-5-[4-(endobicyclo[2.2.1]hept-2-yl)n-butylaminocarbonyl]thiazole;
2-ethylsulfonyl-5-[4-(endobicyclo[3.1.0]-hex-6-yl)n-butylaminocarbonyl]thiazole;
2-ethylsulfonyl-5-[4-(endobicyclo[3.1.0]hex-3-yl)n-butylaminocarbonyl]thiazole;
2-ethylsulfonyl-5-[4-(exobicyclo[3.1.0]hex-2-yl)n-butylaminocarbonyl]thiazole;
2-ethylsulfonyl-5-[4-(4-methylbicyclo[2.2.2]oct-1-yl-n-butylaminocarbonyl]thiazole;
2-ethylsulfonyl-5-[4-adamant-2-yl)n-butylaminocarbonyl]-thiazole;
2-ethylsulfonyl-5-[4-(4-adamant-1-yl)n-butylaminocarbonyl]-thiazole;
2-ethylsulfonyl-5-(but-3-ynylaminocarbonyl)thiazole;
2-ethylsulfonyl-5-(pent-3-nynlaminocarbonyl)thiazole;
2-ethylsulfonyl-5-(hex-3-ynylaminocarbonyl)thiazole;
2-ethylsulfonyl-5-(hept-3-ynylaminocarbonyl)thiazole;
2-ethylsulfonyl-5-(5-methylhex-3-ynylaminocarbonyl)-thiazole;
2-ethylsulfonyl-5-(oct-3-ynylaminocarbonyl)thiazole;
2-ethylsulfonyl-5-(6-methylhept-3-ynylaminocarbonyl)-thiazole;
2-ethylsulfonyl-5-(pent-4-ynylaminocabonyl)thiazole;
2-ethylsulfonyl-5-(hex-4-ynylaminocarbonyl)thiazole;
2-ethylsulfonyl-5-(hept-4-ynylaminocarbonyl)thiazole;
2-ethylsulfonyl-5-(oct-4-ynylaminocarbonyl)thiazole;
2-ethylsulfonyl-5-(6-methylhept-4-ynylaminocarbonyl)-thiazole;
2-ethylsulfonyl-5-(hex-5-ynylaminocarbonyl)thiazole;
2-ethylsulfonyl-5-(hept-5-ynylaminocarbonyl)thiazole;
2-ethylsulfonyl-5-(oct-5-ynylaminocarbonylthiazole;
2-ethylsulfonyl-5(5,5,-dimethylhex-3-ynylaminocarbonyl)thiazole;
2-ethylsulfonyl-5-(methylaminocarbonyl)thiazole;
2-ethylsulfonyl-5-(t-butylaminocarbonyl)thiazole;
2-ethylsulfonyl-5-(hexylaminocarbonyl)thiazole;
2-ethylsulfonyl-5-(4-methylhexylaminocarbonyl)-thiazole;
2-ethylsulfonyl-5-(5-methylhexylaminocarbonyl)-thiazole, nmr (CLCl$_3$) δ: 0.85d, 6H; 1.39;m, 9H, 3.47m, 4H; 6.90s, 1H; 8.34s, 1H;
2-ethylsulfonyl-5-(heptylaminocarbonyl)thiazole;
2-ethylsulfonyl-5-(3-propylheptylaminocarbonyl)-thiazole;
2-ethylsulfonyl-5-(decylaminocarbonyl)thiazole;
2-ethylsulfonyl-5-(dodecylaminocarbonyl)thiazole;
2-ethylsulfonyl-5-(2-cyclopentylethylaminocarbonyl)-thiazole;
2-ethylsulfonyl-5-(2-cyclohexylethylaminocarbonyl)-thiazole;
2-ethylsulfonyl-5-(3-cyclopentylpropylaminocarbonyl)-thiazole;
2-ethylsulfonyl-5-(4-cyclohexylbutylaminocarbonyl)-thiazole;

2-ethylsulfonyl-5-(cycloheptylmethylaminocarbonyl)-thiazole;
-enylaminocarbonyl)thiazole;
2-ethylsulfonyl-5-(4-cyclooctylbutylaminocarbonyl)-thiazole; and Similarly, by following the same procedure but using the corresponding products of Preparation 3 as starting materials, the corresponding 2-methylsulfonyl; 2-t-butylsulfonyl; 2-hexylsulfonyl; and 2-benzylsulfonyl analogs of each of the above compounds are respectively prepared.

EXAMPLE 2A

This example illustrates methods for preparing the compounds of formula I wherein X is —$SO_2R^1$ and Z is $R^4$—CH=CH—$(CH_2)_n$—. In this example a solution of 14 mmoles of sodium periodate in 20 ml. of water is added to a solution of 1.85 mmoles of 2-ethylthio-5-(hex-3-cis-enylaminocarbonyl)-thiazole in 50 ml. of acetic acid. The mixture is heated at 60° C for 19 hours and then poured into water and extracted with methylene chloride (400 ml.). The methylene chloride solution is sequentially washed with water 10% aqueous sodium bicarbonate solution, water and then dried over magnesium sulfate and filtered. The filtrate is then evaporated under vacuum to remove the methylene chloride solvent affording a mixture of 2-ethylsulfonyl-5-(hex-cis-3-enylaminocarbonyl)-thiazole and 2-ethylsulfinyl-5-(hex-cis-3-enylaminocarbonyl)-thiazole as an oily residue. The respective products are then isolated from a sample of the oily residue by thin layer chromatography using ethyl acetate-hexane (1:1 vol.) as the developing solvent. The sulfonyl product is obtained at about Rf 0.5 and the sulfinyl at about Rf 0.2. The remaining portion of the oily residue is used as starting material for Example 4.

Similarly, by following the same procedure but respectively replacing 2-ethylthio-5-(hex-cis-3-enylaminocarbonyl)-thiazole with the corresponding 2-ethylthio products of Preparation 3, the following 2-ethylsulfonyl analogs (and the corresponding sulfinyl-sulfonyl mixtures) are respectively prepared:
2-ethylsulfonyl-5-(hex-5-enylaminocarbonyl)thiazole;
2-ethylsulfonyl-5-(but-3-enylaminocarbonyl)thiazole;
2-ethylsulfonyl-5-(pent-cis-3-enylaminocarbonyl)-thiazole;
2-ethylsulfonyl-5-(hept-cis-3-enylaminocarbonyl)-thiazole;
2-ethylsulfonyl-5-(5-methylhex-cis-3-enylaminocarbonyl)thiazole;
2-ethylsulfonyl-5-(oct-cis-3-enylaminocarbonyl)-thiazole;
2-ethylsulfonyl-5-(6-methylhept-cis-3-enylaminocarbonyl)thiazole;
2-ethylsulfonyl-5-(5,5-dimethylhex-cis-3-enylaminocarbonyl)thiazole;
2-ethylsulfonyl-5-(pent-4-enylaminocarbonyl)thiazole;
2-ethylsulfonyl-5-(6-methylhept-cis-4-enylaminocarbonyl)thiazole;
2-ethylsulfonyl-5-(oct-cis-5-enylaminocarbonyl)-thiazole;
2-ethylsulfonyl-5-(pent-trans-3-enylaminocarbonyl)-thiazole; 2-ethylsulfonyl-5-(hex-trans-3-enylaminocarbonyl) thiazole;
2-ethylsulfonyl-5-(hept-trans-3-enylaminocarbonyl)-thiazole;
2-ethylsulfonyl-5-(5-methylhex-3-enylaminocarbonyl)-thiazole;
2-ethylsulfonyl-5-(oct-trans-3-enylaminocarbonyl)-thiazole;
2-ethylsulfonyl-5-(6-methylhept-trans-3-enylaminocarbonyl)thiazole;
2-ethylsulfonyl-5-(5,5-dimethylhex-trans-3-enylaminocarbonyl)thiazole;
2-ethylsulfonyl-5-(hex-trans-4-enylaminocarbonyl)-thiazole;
2-ethylsulfonyl-5-(oct-trans-4-enylaminocarbonyl)-thiazole;
2-ethylsulfonyl-5-(hept-trans-5-enylaminocarbonyl)-thiazole;

Similarly, by following the same procedure but using the corresponding products of Preparation 3 as starting materials, the corresponding 2-methylsulfonyl; 2-t-butylsulfonyl; 2-hexylsulfonyl; and 2-benzylsulfonyl analogs of each of the above compounds are respectively prepared.

EXAMPLE 3

This example illustrates the process of the invention for preparing 1,2-epoxy-3-(5-substituted aminocarbonylthiazole-2-yloxy)propane. In this example 0.0525 mole of sodium hydride in a 50% mineral oil mixture is stirred in 300 ml. of anhydrous tetrahydrofuran, under nitrogen, then cooled to −30° C and 0.055 mole of glycidol is added dropwise. The mixture is allowed to warm to −5° C and stirred for 10 minutes and then recooled to −30° C. A solution of 0.05 mole of 2-ethylsulfinyl-5-[2-(bicyclo[2.2.1]hept-7-yl)ethylaminocarbonyl]thiazole in 100 ml. of anhydrous tetrahydrofuran is added dropwise and the resulting mixture allowed to warm to 0° C. Additional solvent is added as needed to facilitate stirring. The mixture is maintained for 30 minutes at 0° C and then poured into 500 ml. of ethyl acetate, extracted with 100 ml. of water, and then with 100 ml. of aqueous saturated sodium chloride and dried over anhydrous magnesium sulfate and filtered. The filtrate is evaporated under vacuum affording oily residue which is then further purified by chromatography on silica gel eluting with 40% ethyl acetate-60% hexane, by vol., affording 1,2-epoxy-3-(5-[2-(bicyclo[2.2.1]hept-7-yl)ethylaminocarbonyl]thiazol-2-yloxy)propane.

Similarly, by following the same procedure, the products of Preparation 4 and Example 1 are respectively converted into the corresponding 1,2-epoxy analogs.

EXAMPLE 4

This example illustrates further processes of the invention for preparing the 1,2-epoxypropane compounds of formula B. In this example 0.0525 mole of sodium hydride in a 50% mineral oil mixture is stirred in 300 ml. of anhydrous tetrahydrofuran, under nitrogen, then cooled to −30° C and 0.055 mole of glycidol is added dropwise. The mixture is allowed to warm to −5° C and stirred for 10 minutes and then recooled to −30° C. A solution of 0.05 mole of 2-ethylsulfonyl-5-[2-(adamant-1-yl)ethylaminocarbonyl]thiazole in 100 ml. of anhydrous tetrahydrofuran is added dropwise and the resulting mixture allowed to warm to 0° C. Additional solvent is added as needed to facilitate stirring. The mixture is maintained at 30 minutes at 0° C and then poured into 500 ml. of ethyl acetate, extracted with 100 ml. of water, and then with 100 ml. of aqueous saturated sodium chloride and dried over anhydrous magnesium sulfate and filtered. The filtrate is evaporated under dryness affording oily residue which is then further purified by chromatography on silica gel eluting with 40% ethyl acetate-60% hexane, by vol., affording 1,2-epoxy-3-[5-(2-[adamant-1-yl]ethylaminocarbonyl)-thiazol-2-yloxy]propane.

Similarly, by following the same procedure, the products of Preparation 4 and Examples 2 and 2A are respectively converted into the corresponding 1,2-epoxy analogs.

EXAMPLE 5

This example illustrates the second step of the process of the invention for preparing the compounds of formula C. In this example a mixture containing 12 g. (0.037 mole) of 1,2-epoxy-3-[5-(2-(bicyclo[2.2.1]hept-7-yl]ethylaminocarbonyl)thiazol-2-yloxy]propane, 12 g. (0.164 mole) of t-butylamine and 20 ml. of ethanol is allowed to stand at room temperature for 12 hours. The mixture is then evaporated under vacuum to remove the ethanol solvent and the resulting residue dissolved in 50 ml. of ethyl acetate and cooled to −20° C, and maintained at this temperature for 2 hours. The mixture is then filtered and the resulting filter cake washed with cold (about 0° C) ethyl ether and then recrystallized from ethyl acetate affording 1-t-butylamino-3-(5-[2-(bicyclo[2.2.1]hept-7-yl)ethylaminocarbonyl]thiazol-2-yloxy)propan-2-ol.

Similarly, by following the same procedure but using the products of Examples 3 and 4 as starting materials, the corresponding 1-t-butylamino-5-substituted products of formula C are respectively prepared, for example:
1-t-butylamino-3-(5-[2-(4-methylbicyclo[2.2.2]oct-1-yl)ethylaminocarbonyl]thiazol-2-yloxy)-propan-2-ol, m.p. 141°–142° C;
1-t-butylamino-3-(5-[2-(adamant-2-yl)ethylaminocarbonyl]thiazol-2-yloxy)-propan-2-ol, m.p. 76°–78° C;
1-t-butylamino-3-[5-(hex-5-ynylaminocarbonyl)thiazol-2-yloxy]-propan-2-ol, m.p. 147°–148° C;
1-t-butylamino-3-[5-(hex-3-ynylaminocarbonyl)thiazol-2-yloxy]-propan-2-ol, m.p. 90°–91° C; and
1-t-butylamino-3-[5-(hex-5-enylaminocarbonyl)thiazol-2-yloxy]-propan-2-ol, m.p. 80°–81° C.

EXAMPLE 6

This example illustrates processes of the invention for preparing the compounds of formula C. In this example a mixture containing 12 g. (0.0314 mole) of 1,2-epoxy-3-(5-[2-(adamant-2-yl)ethylaminocarbonyl]thiazol-2-yloxy)propane, 12 g. (0.203 mole) of isopropylamine and 20 ml. of ethanol is allowed to stand at room temperature for 12 hours. The mixture is then evaporated under vacuum to remove the solvent and the resulting residue dissolved in 50 ml. of ethyl acetate and cooled to −20° C, and maintained at this temperature for 2 hours. The mixture is then filtered and the resulting filter cake washed with cold (about 0° C) ethyl ether and then recrystallized from ethyl acetate affording 1-isopropylamino-3-(5-[2-(adamant-2-yl)ethylaminocarbonyl]thiazol-2-yloxy)-propan-2-ol.

Similarly, by following the same procedure but using the products of Examples 3 and 4 as starting materials, the corresponding products of formula C are respectively prepared, for example:
1-isopropylamino-3-(5-[2-(exobicyclo[3.1.0 hex-6-yl)ethylaminocarbonyl]thiazol-2-yloxy)-propan-2-ol, m.p. 128°–130° C; and
1-isopropylamino-3-[5-(5-methylhex-cis-3-enylaminocarbonyl)thiazol-2-yloxy]-propan-2-ol, m.p. 158°–160° C.

EXAMPLE 7

In this example 0.012 mole of sodium hydride (50% mineral oil) is stirred in 50 ml. of tetrahydrofuran; under nitrogen, and 0.02 mole of 5-hydroxymethyl-N-t-butyloxazolidine is added. The mixture is then warmed to 50° C until reaction ceases (about 30 minutes) and then cooled to room temperature. 0.01 Mole of 2-ethylsulfinyl-5-[2-(endobicyclo[3.1.0]hex-6-yl)ethylaminocarbonyl]thiazole in 50 ml. of tetrahydrofuran is then added. The mixture is stirred for four hours at room temperature and then poured into 200 ml. of ethyl acetate, then washed with water; dried over anhydrous magnesium sulfate and filtered. The filtrate is evaporated under vacuum affording a crude residue of 5-(5-[2-(endobicycl[3.1.0]hex-6-yl)ethylaminocarbonyl]thiazol-2-yloxy)methylene-N-5-butyloxazolidine, which is then dissolved in diethyl ether (100 ml.) and hydrogen chloride gas passed over the surface with rapid stirring until no more precipitate is formed. The precipitate is filtered off, washed with ether, then recrystallized from propanol-diethyl ether mixture. The crystals are filtered off and dried under vacuum affording 5-(5-[2-endobicyclo[3.1.0]hex-6-yl)ethylaminocarbonyl]thiazol-2-yloxy)methylene-N-5-butyloxazolidine hydrochoride.

Similarly, by following the same procedure but using the products of Examples 1 and 2 as starting materials, the corresponding compounds of formula E, and their hydrochloride salts, are respectively prepared.

EXAMPLE 8

This example illustrates methods of converting the compounds of formula E into the compounds of formula C. In this example 1 g. of 5-(5-[2-(bicyclo[2.2.1]-hept-7-yl)ethylaminocarbonyl]thiazol-2-yloxy)-methylene-N-t-butyl-2,2-dimethyloxazolidine is dissolved in 50 ml. of ethyl acetate and this solution is treated with aqueous 5% sodium hydroxide (20 ml.) at 20° C. The mixture is allowed to stand for 0.5 hours, washed three times with water, dried over magnesium sulfate and then evaporated to dryness affording 1-t-butyl-3-(5-[2-(bicyclo[2.2.1]hept-7-yl)ethylaminocarbonyl]thiazol-2-yloxy-propan-2-ol.

Similarly, by following the same procedure, the products of Example 5 are respectively hydrolyzed to the corresponding compounds of formula C.

EXAMPLE 9

This example illustrates an alternate method for converting the compounds of formula E to the compounds of formula C. In this example 1 g. of 5-(5-[2-(endobicyclo[3.1.0]hex-6-yl)ethylaminocarbonyl]thiazol-2-yloxy)-methylen-N-t-butyloxazolidine is dissolved in 20 ml. of methanol containing 4 cc of 5% aqueous hydrochloric acid at 20° C. After 15 minutes, the mixture is neutralized with dilute aqueous sodium carbonate solution, poured into water and extracted with ethyl acetate. The ethyl acetate extract is evaporated to dryness yielding 1-t-butylamino-3-(5-[2-(endobicyclo[3.1.0]hex-6-yl)ethylaminocarbonyl]thiazol-2-yloxy)-propan-2-ol.

Similarly, by following the same procedure, the products of Example 5 are respectively hydrolyzed to the corresponding compounds of formula C.

EXAMPLE 10

This example illustrates methods of preparing hydrochloride addition salts of the compound of formula C.

In this example 1 g. of 1-t-butylamino-3-(5-[2-(bicyclo[2.2.1]hept-7-yl)ethylaminocarbonyl]thiazol-2-yloxy)propan-2-ol is dissolved in 10 ml. of ethyl ether at 20° C. A stream of gaseous anhydrous hydrogen chloride is passed over the surface of the solution until the supernatent liquid becomes colorless. The resulting precipitate is collected by filtration, washed with ethyl ether and then crystallized from methanol/diethyl ether, affording crystalline 1-t-butylamino-3-(5-[2-(bicyclo[2.2.1]hept-7-yl)ethylaminocarbonyl]thiazol-2-yloxy)-propan-2-ol hydrochloride, m.p. 161°–166° C.

Similarly, by following the same procedure, the corresponding hydrochloride addition salts of each of the products of Examples 5 and 6 are respectively prepared, for example:

1-isoproplyamino-3-[5-(2-[adamant-2-yl]ethylaminocarbonyl)thiazol-2-yloxy]-propan-2-ol hydrochloride, m.p. 159°–161° C.

EXAMPLE 11

This example illustrates methods of preparing the maleate addition salts of compounds of formula C. In this example one gram of 1-t-butylamino-3-[5-(2-[adamant-1-yl]ethylaminocarbonyl)thiazol-2-yloxy]-propan-2-ol is dissolved in a solution of 5 ml. of ethyl ether and 5 ml. of ethanol at 20° C. To this solution is added 10 ml. of a saturated solution of maleic acid in ethyl ether. The mixtutre is allowed to stand for one hour at room temperature. The resulting precipitate is recovered by filtration, washed three times with ethyl ether and then crystalized from a mixture of ethyl ether and ethanol (1:1) affording crystalline 1-t-butylamino-3-[5-(2-[adamant-1-yl]ethylaminocarbonyl)thiazol-2-yloxy]-propan-2-ol maleate, m.p. 180°–181° C.

Similarly, by following the same procedure, the corresponding maleate addition salts of each of the products of Examples 5 and 6 are respectively prepared, for example:

1-isopropylamino-3-(5-[2-(endobicyclo[3.1.0]hex-6-yl)ethylaminocarbonyl]thiazol-2-yloxy)propan-2-ol maleate, m.p. 136°–138° C;

1-t-butylamino-3-[5-(5-methylhex-3-ynylaminocarbonyl)thiazol-2-yloxy]-propan-2-ol maleate, m.p. 174°–175° C;

1-isopropylamino-3-[5-(methylhex-3-ynylaminocarbonyl)thiazol-2-yloxy]-propan-2-ol maleate, m.p. 152°–153° C;

1-isopropylamino-3-[5-(hex-cis-3-enylaminocarbonyl)-2-thiazolyloxy]-propan-2-ol maleate, m.p. 165°–165° C; and 1-isopropylamino-3-[5-(hex-trans-3-enylaminocarbonyl)-2-thiazolyloxy]-propan-2-ol maleate, m.p. 164°–165° C.

Obviously many modifications and variations of the invention, described hereinabove and below in the claims, can be made without departing from the essence and scope thereof.

What is claimed is:

1. A compound having the formula

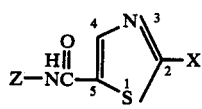

(I)

wherein X is the group —$SOR^1$ or —$SO_2R^1$ wherein $R^1$ is lower alkyl, phenyl, or benzyl and Z is selected from the group of alkyl having from one through 12 carbon atoms, and groups having the formulas:

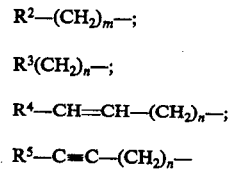

wherein $m$ is 1, 2, 3, or 4; $n$ is 2, 3, or 4; $R^2$ is cycloalkyl having from three through eight carbon atoms; $R^3$ is selected from the group of bicyclo[3.1.0]hexyl; bicyclo[2.2.1]heptyl; adamantyl; and 4-methylbicyclo[2.2.2-]oct-1-yl and wherein attachment to the $(CH_2)_n$ linking group can be at any ring atom of bicyclo[3.1.0]hexyl; bicyclo[2.2.1]heptyl and adamantyl group and is at the 1-position of the 4-methylbicyclo[2.2.2]octyl group; and $R^4$ and $R^5$ are hydrogen or alkyl having from one through four carbon atoms and wherein the groups $R^4$—CH=CH—$(CH_2)_n$— and $R^5$—C≡C—$(CH_2)_n$— each have from four through eight carbon atoms.

2. The compound of claim 1 wherein $R^1$ is methyl, ethyl or benzyl.

3. The compound of claim 1 wherein Z is alkyl.

4. The compound of claim 3 wherein Z is 5-methylhexyl.

5. The compound of claim 4 wherein $R^1$ is methyl, ethyl or benzyl.

6. The compound of claim 1 wherein Z is the group having the formula $R^2$—$(CH_2)_m$— wherein m and $R^2$ are as defined in claim 1.

7. The compound of claim 6 wherein Z is cyclopentylethyl; or cyclohexylethyl.

8. The compound of claim 7 wherein $R^1$ is methyl, ethyl or benzyl.

9. The compound of claim 1 wherein Z is the group having the formula $R^3(CH_2)_n$— wherein n and $R^3$ are as defined in claim 1.

10. The compound of claim 9 wherein n is 2 and $R^3$ is endobicyclo[3.1.0]hex-6-yl; endobicyclo[3.1.0 hex-3-yl; bicyclo[2.2.1]hept-7-yl; or adamant-2-yl.

11. The compound of claim 10 wherein $R^1$ is methyl, ethyl or benzyl.

12. The compound of claim 1 wherein Z is the group having the formula $R^4$—CH=CH—$(CH_2)_n$— wherein n and $R^4$ are as defined in claim 1.

13. The compound of claim 12 wherein Z is 5-methylhex-cis-3-enyl; hex-cis-3-enyl; 5-methylhex-trans-3enyl or hex-trans-3-enyl.

14. The compound of claim 13 wherein $R^1$ is methyl, ethyl or benzyl.

15. The compound of claim 1 wherein Z is the group having the formula $R^5$—C≡C—$(CH_2)_n$— wherein $R^5$ and n are as defined in claim 1.

16. The compound of claim 15 wherein Z is 5-methylhex-3-ynyl or hex-3-ynyl.

17. The compound of claim 16 wherein $R^1$ is methyl, ethyl or benzyl.

18. The compound of claim 1 wherein X is the group having the formula —$SOR^1$ wherein $R^1$ is as defined in claim 1.

19. The compound of claim 1 wherein X is the group having the formula —$SO_2R^1$ wherein $R^1$ is as defined in claim 1.

* * * * *